United States Patent
Orr et al.

(10) Patent No.: US 10,085,674 B2
(45) Date of Patent: Oct. 2, 2018

(54) METHOD AND APPARATUS FOR MONITORING AND CONTROLLING A PRESSURE SUPPORT DEVICE

(75) Inventors: Joseph Allen Orr, Park City, UT (US); Christina Marie Long, Salt Lake City, UT (US)

(73) Assignee: Koninklijke Philips N.V., Eindhoven (NL)

( * ) Notice: Subject to any disclaimer, the term of this patent is extended or adjusted under 35 U.S.C. 154(b) by 1078 days.

(21) Appl. No.: 14/241,577

(22) PCT Filed: Sep. 14, 2012

(86) PCT No.: PCT/IB2012/054814
§ 371 (c)(1),
(2), (4) Date: Feb. 18, 2015

(87) PCT Pub. No.: WO2013/042024
PCT Pub. Date: Mar. 28, 2013

(65) Prior Publication Data
US 2015/0173647 A1    Jun. 25, 2015

Related U.S. Application Data

(60) Provisional application No. 61/537,655, filed on Sep. 22, 2011.

(51) Int. Cl.
*A61B 5/08* (2006.01)
*A61M 16/16* (2006.01)
(Continued)

(52) U.S. Cl.
CPC .......... *A61B 5/082* (2013.01); *A61M 16/024* (2017.08); *A61M 16/161* (2014.02);
(Continued)

(58) Field of Classification Search
CPC ..... A61B 5/082; A61M 16/12; A61M 16/161; A61M 16/202; A61M 2016/0027;
(Continued)

(56) References Cited

U.S. PATENT DOCUMENTS 2,830,583 A * 4/1958 Finney, Jr. ............... A62B 9/00
128/204.21
3,215,057 A * 11/1965 Turek .................... A61M 16/12
454/70
(Continued)

FOREIGN PATENT DOCUMENTS

| CN | 1777454 A | 5/2006 |
| CN | 101111277 A | 1/2008 |

(Continued)

*Primary Examiner* — William McCalister

(57) ABSTRACT

A system is configured to generate a pressurized flow of gas comprised of a first gas having a partial pressure that varies in a predetermined manner. This may be used, for example, to simulate a previous and/or theoretical respiratory gas flow that was produced (or could have been produced) by a subject. The system is configured to deliver the pressurized flow of gas to a testing system configured to measure the partial pressure the first gas in flows of gas. This may provide an opportunity to determine the response of individual testing systems to various clinical circumstances.

14 Claims, 3 Drawing Sheets

(51) Int. Cl.
*A61M 16/20* (2006.01)
*G05D 11/13* (2006.01)
*A61M 16/12* (2006.01)
*G01N 33/00* (2006.01)
*A61M 16/00* (2006.01)
*A61M 16/10* (2006.01)

(52) U.S. Cl.
CPC ........... *A61M 16/202* (2014.02); *A61M 16/12* (2013.01); *A61M 2016/0027* (2013.01); *A61M 2016/0033* (2013.01); *A61M 2016/102* (2013.01); *A61M 2205/3368* (2013.01); *A61M 2209/02* (2013.01); *A61M 2230/43* (2013.01); *G01N 2033/0072* (2013.01); *G05D 11/132* (2013.01); *Y10T 137/2499* (2015.04); *Y10T 137/2529* (2015.04); *Y10T 137/2703* (2015.04); *Y10T 137/87684* (2015.04)

(58) Field of Classification Search
CPC .... A61M 2016/0033; A61M 2016/102; A61M 2016/3368; A61M 2016/02; A61M 2016/43; G01N 2033/0072; G05D 11/132; Y10T 137/2499; Y10T 137/2529; Y10T 137/2703; Y10T 137/87684
USPC ........................... 137/88, 101.19, 87.03, 606
See application file for complete search history.

(56) References Cited

U.S. PATENT DOCUMENTS

| | | | | |
|---|---|---|---|---|
| 3,593,735 A | * | 7/1971 | Reiher | A62B 7/14 128/204.22 |
| 3,672,388 A | * | 6/1972 | Ringwall | F15C 1/005 128/201.27 |
| 3,722,510 A | * | 3/1973 | Parker | B63C 11/24 128/205.12 |
| 3,727,626 A | * | 4/1973 | Kanwisher | A61M 16/12 128/201.27 |
| 4,057,205 A | * | 11/1977 | Vensel | B64D 13/02 137/88 |
| 5,157,957 A | * | 10/1992 | Mettes | B01F 3/026 137/7 |
| 5,239,856 A | | 8/1993 | Mettes et al. | |
| 5,611,845 A | * | 3/1997 | Delp, II | B01D 53/22 96/10 |
| 5,887,611 A | * | 3/1999 | Lampotang | A61M 16/12 137/101.19 |
| 5,915,834 A | * | 6/1999 | McCulloh | A61M 16/12 128/204.22 |
| 6,463,930 B2 | | 10/2002 | Biondi et al. | |
| 2004/0079372 A1 | | 4/2004 | Erwin et al. | |
| 2007/0044796 A1 | | 3/2007 | Zdrojkowski et al. | |
| 2007/0062533 A1 | | 3/2007 | Choncholas et al. | |
| 2007/0169779 A1 | | 7/2007 | Freeman | |
| 2008/0000471 A1 | * | 1/2008 | Bolam | A61M 16/12 128/200.24 |
| 2011/0120471 A1 | * | 5/2011 | Freeman | A61M 16/12 128/204.23 |
| 2015/0173647 A1 | * | 6/2015 | Orr | A61B 5/082 434/262 |

FOREIGN PATENT DOCUMENTS

| | | |
|---|---|---|
| CN | 101394385 A | 3/2009 |
| CN | 101450237 A | 6/2011 |
| CN | 102107037 A | 6/2011 |
| JP | 2007195977 A | 8/2007 |
| JP | 2009090141 A | 4/2009 |
| JP | 2010521243 A | 6/2010 |
| WO | 2010136923 A1 | 12/2010 |

* cited by examiner

METHOD AND APPARATUS FOR MONITORING AND CONTROLLING A PRESSURE SUPPORT DEVICE

CROSS-REFERENCE TO PRIOR APPLICATIONS

This application is the U.S. National Phase application under 35 U.S.C. § 371 of International Application No. PCT/IB2012/054814, filed on Sep. 14, 2012, which claims the benefit of U.S. Provisional Patent Application No. 61/537,655, filed on Sep. 22, 2011. These applications are hereby incorporated by reference herein.

BACKGROUND

1. Field

The present disclosure pertains to a method and apparatus for generating predetermined pressurized flows of gas, and, in particular, to generating pressurized flows of gas that simulate respiratory gas flows.

2. Description of the Related Art

A variety of different systems adapted to determine information related to the composition of respiratory gas flows are known. These systems are generally adapted to receive a flow of gas from the airway of a subject (e.g., through a respiratory circuit), and to monitor the partial pressure of one or more molecular species present in the gas. Such systems include, for example, capnometers, respiratory oxygen sensors, and/or other systems.

Different systems may produce results that vary for gas flows with similar compositions. Similarly, clinicians, care providers, and/or other users may misinterpret the results produced by these systems due to inexperience and/or unfamiliarity to how a system will react to a given subject type, therapy setting, and/or condition.

SUMMARY

Accordingly, one or more aspects of the present disclosure relate to a system configured to generate a pressurized flow of gas comprised of a first gas having a partial pressure that varies in a predetermined manner. In some embodiments, the system comprises electronic storage, an outlet, a flow generator, and one or more processors. The electronic storage stores a gas flow data set that specifies a pressurized flow of gas, the gas flow data set specifying partial pressure of a first gas in the pressurized flow of gas as a function of time. The outlet is configured to emit a pressurized flow of gas. The flow generator comprises a baseline valve assembly configured to control a flow rate of a baseline gas through the outlet; and a first valve assembly configured to control a flow rate of the first gas through the outlet. The one or more processors are configured to execute a baseline flow rate module, a first flow rate module, and a control module. The baseline flow rate module is configured to obtain a baseline flow rate for the baseline gas during generation of the pressurized flow of gas, wherein the baseline flow rate is a function of a parameter of the partial pressure specified for the first gas by the gas flow data set. The first flow rate module is configured to determine a first flow rate for the first gas based on the partial pressure specified for the first gas by the gas flow data set such that the first flow rate changes over time in accordance with the partial pressure specified for the first gas by the gas flow data set. The control module is configured to control the flow generator to generate the pressurized flow of gas specified by the gas flow data set, including controlling the baseline valve assembly to deliver the baseline gas to the outlet at the baseline flow rate and controlling the first valve assembly to deliver the first gas to the outlet at the first flow rate.

Yet another aspect of the present disclosure relates to a method of generating a pressurized flow of gas comprised of a first gas having a partial pressure that varies in a predetermined manner. In some embodiments, the method comprises storing a gas flow data set that specifies a pressurized flow of gas, the gas flow data set specifying partial pressure of a first gas in the pressurized flow of gas as a function of time; and generating the pressurized flow of gas in accordance with the gas flow data set such that the partial pressure of the first gas varies over time as specified in the gas flow data set. In some embodiments, generating the pressurized flow of gas comprises obtaining a baseline flow rate for a baseline gas during generation of the pressurized flow of gas, wherein the baseline flow rate is a function of a parameter of the partial pressure specified for the first gas by the gas flow data set; determining a first flow rate for the first gas based on the partial pressure specified for the first gas by the gas flow data set such that the first flow rate changes over time in accordance with the partial pressure specified for the first gas by the gas flow data set; and delivering the baseline gas at the baseline flow rate and the first gas at the first flow rate to create the pressurized flow of gas specified by the gas flow data set Still another aspect of present disclosure relates to a system for generating a pressurized flow of gas comprised of a first gas having a partial pressure that varies in a predetermined manner. In some embodiments, the system comprises means for storing a gas flow data set that specifies a pressurized flow of gas, the gas flow data set specifying partial pressure of a first gas in the pressurized flow of gas as a function of time; and means for generating the pressurized flow of gas in accordance with the gas flow data set such that the partial pressure of the first gas varies over time as specified in the gas flow data set. In some embodiments, means for generating the pressurized flow of gas comprises means for obtaining a baseline flow rate for a baseline gas during generation of the pressurized flow of gas, wherein the baseline flow rate is a function of a parameter of the partial pressure specified for the first gas by the gas flow data set; means for determining a first flow rate for the first gas based on the partial pressure specified for the first gas by the gas flow data set such that the first flow rate changes over time in accordance with the partial pressure specified for the first gas by the gas flow data set; and means for delivering the baseline gas at the baseline flow rate and the first gas at the first flow rate to create the pressurized flow of gas specified by the gas flow data set.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
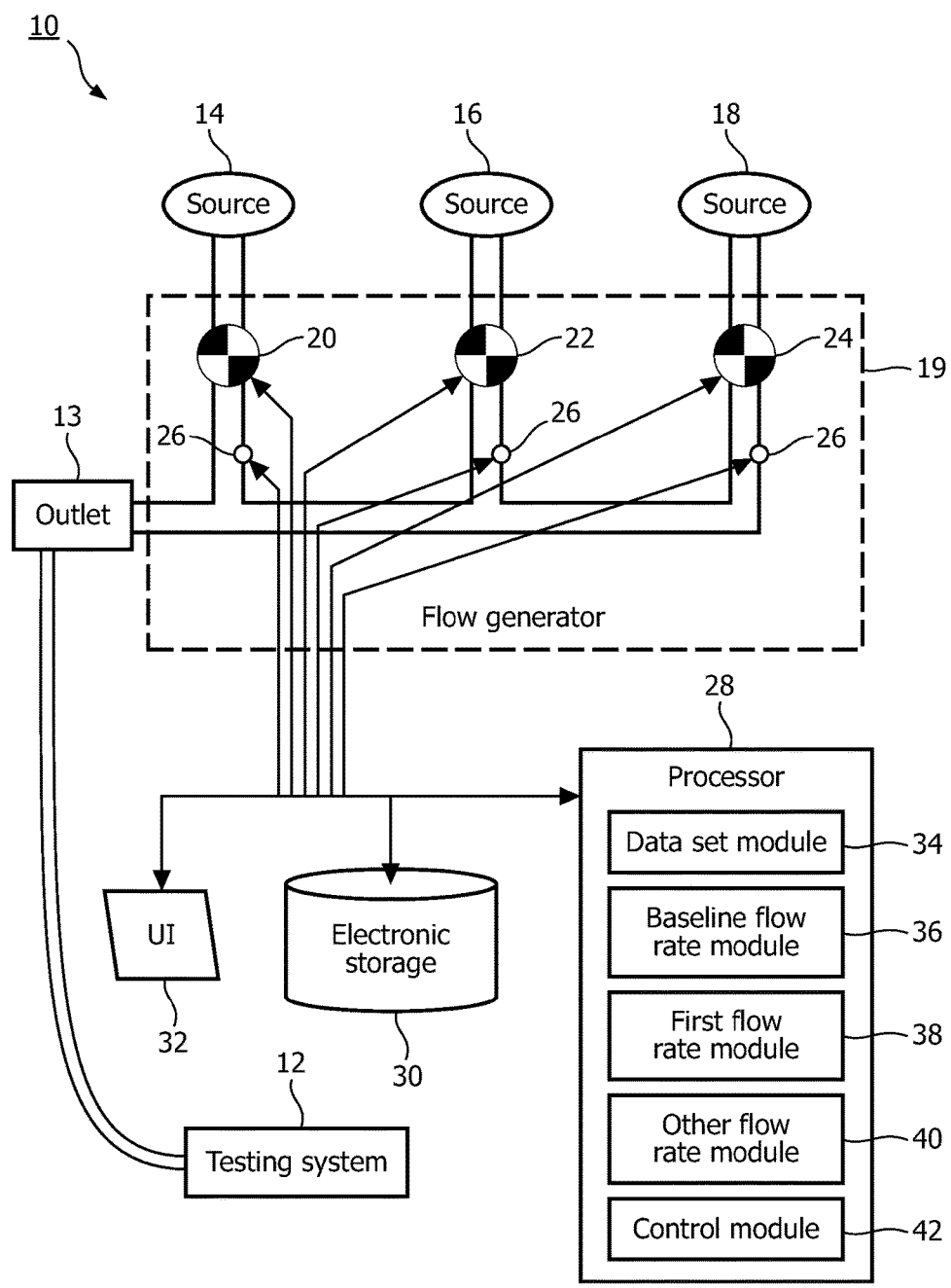
FIG. 1 illustrates a system configured to generate a pressurized flow of gas having a partial pressure of a first gas that varies according to time in a predetermined manner.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to generate a pressurized flow of gas comprised of a first gas having a partial pressure that varies in a predetermined manner. System 10 may be used, for example, to simulate a previous and/or theoretical respiratory gas flow that was produced (or could have been produced) by a subject. System 10 is configured to deliver the pressurized flow of gas to a testing system 12. Testing system 12 is configured to measure the partial pressure the first gas in flows of gas. For example, testing system 12 may include one or more of a capnometer, an oxygen measuring system, and/or other systems configured to measure one or more molecular species present in gas flows (e.g., respiratory gas flows and/or other gas flows). The pressurized flow of gas generated by system 10 may provide an opportunity to determine the response of individual testing systems, such as testing system 12, to various clinical circumstances. As can be seen in FIG. 1, system 10 may include one or more of an outlet 13, a set of gas sources (illustrated as a baseline gas source 14, a first gas source 16, and an other gas source 18), a flow generator 19, one or more sensors 26, one or more processors 28, electronic storage 30, a user interface 32, and/or other components.

Outlet 13 is configured to emit pressurized flows of gas generated by system 10. Outlet 13 is configured to interface with testing system 12 such that pressurized flows of gas generated by system 10 are delivered to testing system 12 in the same manner that gas would be delivered to testing system 12 during typical use. As an exemplary embodiment, if testing system 12 is configured to monitor levels of one or more gases present in respiratory gas being breathed by a subject, outlet 13 may be configured to interface with testing system 12 in the same manner that testing system 12 would interface with a respiratory circuit to receive respiratory gas therefrom. For example, outlet 13 may include an interface element (e.g., a nozzle, a clip, a spout, and/or other interface elements) configured to connect to testing system 12 in the same manner that a respiratory circuit would.

Gas sources 14, 16, and 18 are configured to provide gas to system 10. The gas provided by baseline gas source 14, first gas source 16 and/or other gas source 18 may be pressurized. Individual ones of gas sources 14, 16, and/or 18 may include a canister, a Dewar, a wall gas source, an extraction and/or purification system, and/or other sources of gas.

Baseline gas source 14 is configured to provide a baseline gas to system 10. The baseline gas provides a "background" gas level so that a first gas and/or other gases can be combined with the baseline gas at appropriate partial pressure(s). As such, the baseline gas may be substantially free from the first gas and/or the other gases. By way of non-limiting example, in some embodiments, the baseline gas is nitrogen.

First gas source 16 is configured to provide the first gas to system 10. As was mentioned above, the partial pressure of the first gas is varied as a function of time in the pressurized flow of gas generated by system 10. The first gas is a gas that testing system 12 is configured to monitor. As such, varying the partial pressure of the first gas in the pressurized flow of gas generated by system 10 will be reflected in the output of testing system 12. By way of non-limiting example, the first gas may include carbon dioxide, oxygen, nitrous oxide, anesthetic vapor such as isoflurane, and/or other gases.

In some embodiments, system 10 may include one or more other gases with partial pressures that are varied in the pressurized flow of gas in a predetermined manner. This may be used, for example, to simulate the variation of two separate gases in respiratory output of a subject (e.g., carbon dioxide and oxygen, and/or other combinations of gases). In such embodiments, other gas source 18 is configured to provide an other gas to system 10. The illustration of system 10 as being capable of including one other gas in the pressurized flow of gas is not intended to be limiting. System 10 may be configured to include a plurality of other gases in the pressurized flow of gas with partial pressures that vary over time independently from the first gas, or system 10 may not include any other such gases in the pressurized flow of gas (e.g., system 10 may be configured without other gas source 18 and/or other valve assembly 24).

Flow generator 19 is configured to generate pressurized flows of gas. This includes generating pressurized flows of gas having predetermined proportions of the gases provided by the gas sources 14, 16, and/or 18. Flow generator 19 may include one or more of a baseline valve assembly 20, a first valve assembly 22, other valve assembly 24, and/or other components. In embodiments in which one or more of the gas sources 14, 16, and/or 18 is not pressurized, flow generator 19 may include a pressure generator (not shown) for pressurizing such gas. The pressure generator may include, for example, a blower, an impeller, a bellows, and/or other pressure generators.

Baseline valve assembly 20 is configured to control a flow rate of the baseline gas (e.g., from baseline gas source 14) through outlet 13. Baseline valve assembly 20 includes one or more valves that controllably permit baseline gas to flow from baseline gas source 14 to outlet 13. Baseline valve assembly 20 may include plurality of valves that are individually controllable to open separate pathways from baseline gas source 14 to outlet 13. By controlling the plurality of valves in a coordinated manner, the overall flow rate of baseline gas through outlet 13 can be controlled. Baseline valve assembly 20 may include one or more valves that define individual flow paths that can be separately controlled over a range of flow rates. The range of flow rates for a given valve may go from zero to some maximum flow rate for the given valve. By way of non-limiting example, baseline valve assembly 20 may include one or more of a solenoid valve, stepper or continuous motor controlled needle valve, piezo crystal valve, and/or other valves.

First valve assembly 22 is configured to control a flow rate of the first gas through outlet 13. First valve assembly 22 includes one or more valves that define individual flow paths that can separately be controlled over a range of flow rates. The range of flow rates for a given valve may go from zero to some maximum flow rate for the given valve. As such, an assembly range of flow rates for first valve assembly 22 as a whole may from some assembly minimum flow rate (e.g., zero) to some assembly maximum flow rate. By way of example, first valve assembly 22 may include one or more of a solenoid valve, stepper or continuous motor controlled needle valve, piezo crystal valve, and/or other valves.

The valve(s) included in first valve assembly 22 may not have linear responses to applied current and/or voltage. Further, such valves may experience hysteresis and/or other sources of imprecision and/or inaccuracy. Such non-linearity and/or other phenomena may complicate controlling first valve assembly 22 dynamically to simulate a pressurized flow of gas having a partial pressure of the first gas that varies over time. Within the assembly range of flow rates, there may be a range portion for which non-linearity and/or other phenomena complicating control of first valve assembly 22 may be relatively low. This range portion of the overall assembly range of flow rates may be referred to as the operational range of flow rates for first valve assembly 22. In some embodiments, the operational range for first valve assembly 22 may include flow rates of relatively low magnitude. By way of non-limiting example, the operational range of first valve assembly 22 may be from about zero to about 10 liters per minute.

Other valve assembly 24 is configured to control a flow rate of the other gas through outlet 13 in embodiments in which the pressurized flow of gas includes one or more gases in addition to the first gas and the base gas. Other valve assembly 24 may be formed and/or operated in substantially the same manner as first valve assembly 22.

Sensors 26 may be configured to generate output signals conveying information related to gas parameters of gas within system 10. Such gas may include gas passing through baseline valve assembly 20, gas passing through first valve assembly 22, gas passing through other valve assembly 24, the pressurized flow of gas upstream from outlet 13, and/or other gas. The gas parameters may include one or more of pressure, flow rate, temperature, humidity, composition, and/or other gas parameters. The output signals generated by sensors 26 may be implemented in the control of baseline valve assembly 20, first valve assembly 22, and/or other valve assembly 24 (e.g., in a feedback manner), to verify output of testing system 12, to track accuracy and/or precision in simulating a pressurized flow of gas, and/or for other purposes. It will be appreciated that the number and/or location of sensors 26 illustrated in FIG. 1 is not intended to be limiting. Sensors 26 could include any number of sensing devices disposed upstream and/or downstream from one or more of baseline valve assembly 20, first valve assembly 22, other valve assembly 24, and/or outlet 13.

Processor 28 may be configured to execute one or more processing modules. The processing modules may include one or more of data set module 34, a baseline flow rate module 36, a first flow rate module 38, one or more other flow rate modules 40, a control module 42, and/or other modules. Processor 28 may be configured to execute modules 34, 36, 38, 40, and/or 42 by software; hardware; firmware; some combination of software, hardware, and/or firmware; and/or other mechanisms for configuring processing capabilities on processor 28.

Data set module 34 is configured to obtain a gas flow data set. The gas flow data set specifies a pressurized flow of gas to be generated by system 10. Specifying the pressurized flow of gas includes partial pressure of the first gas in the pressurized flow of gas as a function of time. The gas flow data set may further specify partial pressures of one or more other gases in the pressurized flow of gas as a function of time. By way of non-limiting example, the gas flow data set may represent a plot of partial pressure for the first gas with respect to time. The gas flow data set may include, for example, a previously recorded partial pressure plot for the first gas in a respiratory gas flow of a subject. The partial pressure plot may have been taken as the subject was exhibiting some type of respiratory phenomenon, state, event, or other respiratory circumstance (e.g., intensive care, sedation, operating room, and/or other circumstances). The subject may be a certain type of subject (e.g., adult, pediatric, neonatal, and/or other subject types), may suffer from a specific disease or condition (e.g., hypoventilation, ventilation perfusion mismatch, and/or other conditions), and/or may be of interest for other reasons. The gas flow data set may be selected such that generation of the specified pressurized flow of gas by system 10 will facilitate testing, refinement, and/or development of testing system 12 (or some component thereof) and/or a user of testing system 12 (e.g., as training for a clinician, researcher, or careprovider).

As used herein, the term "partial pressure" is not limited to the pressure of an individual molecular species if it alone occupied a given volume. Instead, the term "partial pressure" is intended to encompass any measurement that indicates an amount of a molecular species in relation to the gas mixture of which it is a part. Such measurements may include concentration, composition, and/or other measurements.

Baseline flow rate module 36 is configured to obtain a baseline flow rate for the baseline gas during generation of the pressurized flow of gas. For the pressurized flow of gas, the baseline flow rate is a function of a parameter of the partial pressure for the first gas. The parameter may reflect the magnitude of the partial pressure for the first gas over the pressurized flow of gas. By way of non-limiting example, the parameter may include one or more of a maximum partial pressure, a mean partial pressure, a median partial pressure, peak partial pressure, frequency of partial pressure variation, and/or other parameters. Obtaining the baseline flow rate may include determining the baseline flow rate, accessing a previously determined baseline flow rate (e.g., previously stored with the gas flow data set), receiving the baseline flow rate from an external source (e.g., a user via user interface 32, a processor or electronic storage external to system 10, and/or other sources). The baseline flow rate may be a fixed value for the pressurized flow of gas, and/or the baseline flow rate may fluctuate as a function of time during generation of the pressurized flow of gas.

The baseline flow rate is determined based on the parameter of the partial pressure for the first gas in order to enhance the operation of first valve assembly 22 during the generation of the pressurized flow of gas. As was mentioned above, the valve(s) included in first valve assembly 22 may not respond linearly to an applied potential and/or current, may experience hysteresis, and/or may be susceptible to other phenomena that would detract from the accuracy and/or precision of system 10 in generating the pressurized flow of gas in accordance with the gas flow data set. These phenomena may be relatively more impactful if first valve assembly 22 is operated outside of its operational range of flow rates. Determination of baseline flow rate based on the parameter of the partial pressure for the first gas is performed to reduce inaccuracy and/or imprecision caused by operating first valve assembly 22 outside of its operational range in generating the pressurized flow of gas. For example, the baseline flow rate may be determined so that operation of first valve assembly 22 is kept within its operational range over the entire range of partial pressures for the first gas specified by the gas flow data set, so that operation of first valve assembly 22 is kept primarily within its operational range over the entire range of partial pressures for the first gas specified by the gas flow data set, so that operation of first valve assembly 22 outside of its operational range is minimized over the entire range of partial pressures for the first gas specified by the gas flow data set, and/or to otherwise control how much of pressurized flow of gas is generated with first valve assembly 22 operating outside of its operational range.

In embodiments, one or more other gases will be included in pressurized flow of gas with the first gas and the baseline gas. In such embodiments, the gas flow data set may specify a partial pressure for an other gas that varies over time. Baseline flow rate module 36 is configured such that the obtained baseline flow rate also controls how much of pressurized flow of gas is generated with other valve assembly 24 operating outside of its operational range.

First flow rate module 38 is configured to determine a first flow rate for the first gas during generation of the pressurized flow of gas. The determination of the first flow rate is made based on the partial pressure specified for the first gas by the gas flow data set. As such, the first flow rate changes over time in accordance with the variations in partial pressure for the first gas specified by the gas flow data set.

Other flow rate modules 40 are configured to determine flow rates for the one or more other gases (if applicable). The determination of a flow rate by one of other flow rate modules 40 for a corresponding other gas may be performed in substantially the same manner as the determination of the first flow rate by first flow rate module 38.

Control module 42 is configured to control flow generator 19 to generate the pressurized flow of gas specified by the gas flow data set. This includes controlling baseline valve assembly 20 so that the baseline gas is delivered to outlet 13 at the baseline flow rate, and controlling first valve assembly 22 so that the first gas is delivered to outlet 13 at the first flow rate.

Figure 2:
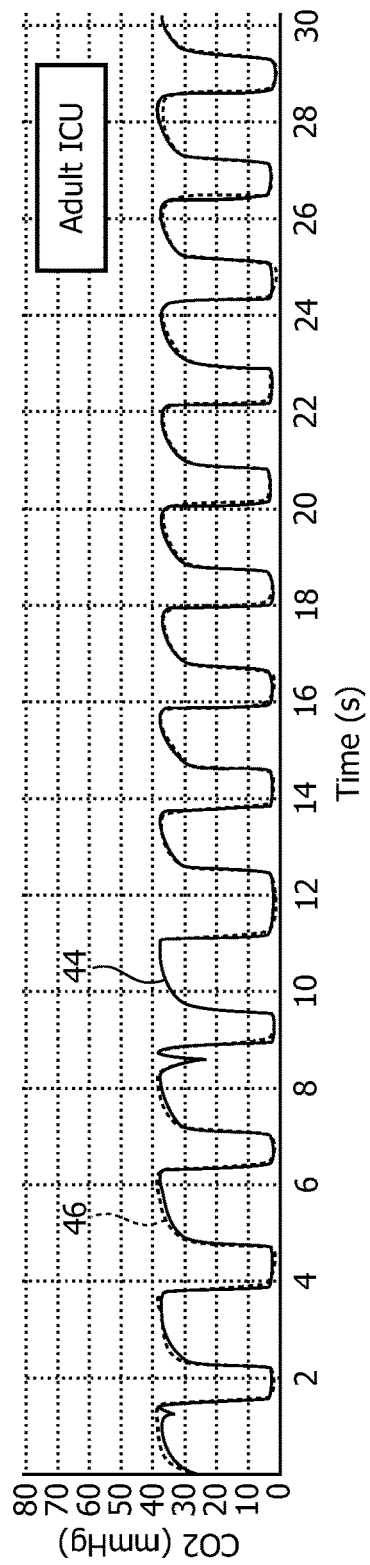
FIG. 2 illustrates a plot of a partial pressure of a first gas in a respiratory gas flow and a simulation of the respiratory gas flow.

By way of illustration, FIG. 2 illustrates graphically a first pressurized flow of gas plot 44 specified by a first gas flow data set. In particular, plot 44 represents partial pressure of a first gas (e.g., carbon dioxide) as a function of time during respiration of a subject. Specifically, the subject is an adult in an Intensive Care Unit. FIG. 2 further illustrates a first simulated pressurized flow of gas plot 46. Plot 46 represents partial pressure of the first gas during generation of a simulated pressurized flow of gas performed (e.g., by a system similar to or the same as system 10 shown in FIG. 1) based on the first gas flow data set.

Figure 3:
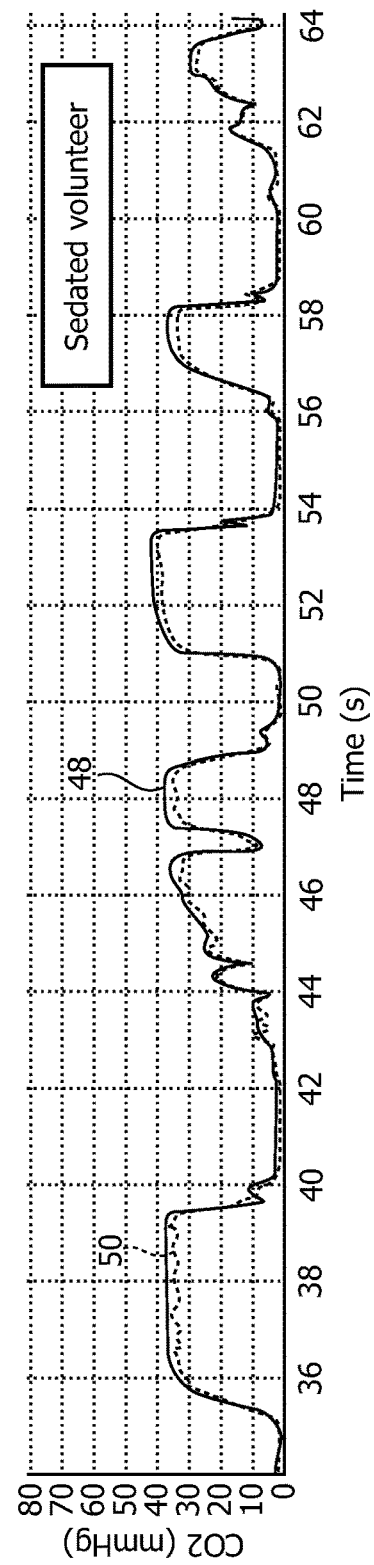
FIG. 3 illustrates a plot of a partial pressure of a first gas in a respiratory gas flow and a simulation of the respiratory gas flow.

Similarly, FIG. 3 illustrates a second pressurized flow of gas plot 48 specified by a second gas flow data set. Plot 48 represents partial pressure of a first gas (e.g., carbon dioxide) as a function of time during respiration of a subject. In particular, the subject has been sedated, causing erratic respiration shown in plot 48. FIG. 3 further illustrates a second simulated pressurized flow of gas plot 50. Plot 50 represents partial pressure of the first gas during generation of a simulated pressurized flow of gas performed (e.g., by a system similar to or the same as system 10 shown in FIG. 1) based on the second gas flow data set.

Referring back to FIG. 1, processor 28 may include one or more of a digital processor, an analog processor, a digital circuit designed to process information, an analog circuit designed to process information, a state machine, and/or other mechanisms for electronically processing information. Although processor 28 is shown in FIG. 1 as a single entity, this is for illustrative purposes only. In some implementations, processor 28 may include a plurality of processing units. These processing units may be physically located within the same device, or processor 28 may represent processing functionality of a plurality of devices operating in coordination.

It should be appreciated that although modules 34, 36, 38, 40, and 42 are illustrated in FIG. 1 as being co-located within a single processing unit, in implementations in which processor 38 includes multiple processing units, one or more of modules 34, 36, 38, 40, and/or 42 may be located remotely from the other modules. The description of the functionality provided by the different modules 34, 36, 38, 40, and/or 42 described below is for illustrative purposes, and is not intended to be limiting, as any of modules 34, 36, 38, 40, and/or 42 may provide more or less functionality than is described. For example, one or more of modules 34, 36, 38, 40, and/or 42 may be eliminated, and some or all of its functionality may be provided by other ones of modules 34, 36, 38, 40, and/or 42. As another example, processor 38 may be configured to execute one or more additional modules that may perform some or all of the functionality attributed below to one of modules 34, 36, 38, 40, and/or 42.

Electronic storage 30 comprises electronic storage media that electronically stores information. The electronic storage media of electronic storage 30 may include one or both of system storage that is provided integrally (i.e., substantially non-removable) with system 10 and/or removable storage that is removably connectable to system 10 via, for example, a port (e.g. RS232 serial, a USB port, a firewire port, etc.) or a drive (e.g., a disk drive, etc.). Electronic storage 30 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 30 may include virtual storage resources, such as storage resources provided via a cloud and/or a virtual private network. Electronic storage 30 may store software algorithms, information determined by processor 28, information received via user interface 32, gas flow data sets, and/or other information that enables system 10 to function properly. Electronic storage 30 may be a separate component within system 30, or electronic storage 30 may be provided integrally with one or more other components of system 10 (e.g., processor 28).

User interface 32 is configured to provide an interface between system 10 and one or more users through which the users may provide information to and receive information from system 10. This enables data, results, and/or instructions and any other communicable items, collectively referred to as "information," to be communicated between the users and system 10. Examples of interface devices suitable for inclusion in user interface 32 include a keypad, buttons, switches, a keyboard, knobs, levers, a display screen, a touch screen, speakers, a microphone, an indicator light, an audible alarm, and a printer. In one embodiment, the functionality of which is discussed further below, user interface 30 actually includes a plurality of separate interfaces.

It is to be understood that other communication techniques, either hard-wired or wireless, are also contemplated by the present invention as user interface 32. For example, the present invention contemplates that user interface 32 may be integrated with a removable storage interface provided by electronic storage 30. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 32 include, but are not limited to, an RS-232 port, RF link, an IR link, modem (telephone, cable or other). In short, any technique for communicating information with system 10 is contemplated by the present invention as user interface 32.

Figure 4:
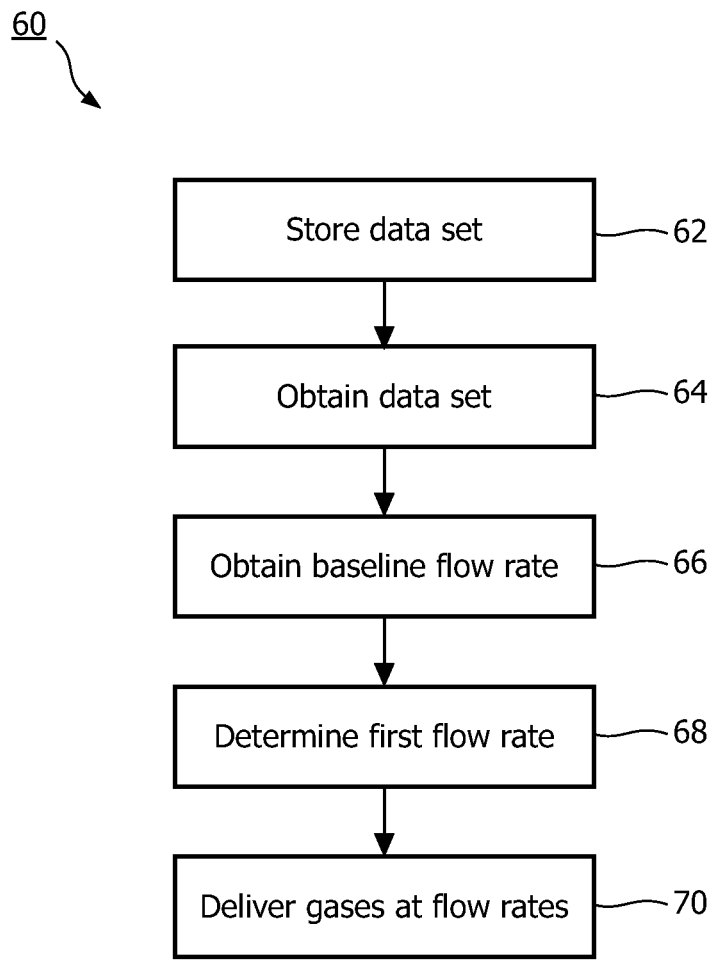
FIG. 4 illustrates a method of generating a pressurized flow of gas having a partial pressure of a first gas that varies according to time in a predetermined manner.

FIG. 4 illustrates a method 60 of generating a pressurized flow of gas having a partial pressure of a first gas that varies according to time in a predetermined manner. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 4 and described below is not intended to be limiting.

In some embodiments, method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, a gas flow data set is stored. The gas flow data set specifies a pressurized flow of gas. This includes specifying partial pressure of a first gas in the pressurized flow of gas as a function of time.

At an operation 64, the gas flow data set is obtained. In some embodiments, operation 64 is performed by a data set module similar to or the same as data set module 34 (shown in FIG. 1 and described above).

At an operation 66, a baseline flow rate for a baseline gas during generation of the pressurized flow of gas is obtained. Obtaining the baseline flow rate may include determining the baseline flow rate, receiving the baseline flow rate, accessing the baseline flow rate, and/or obtaining the baseline flow rate in other ways. The baseline flow rate has been determined as a function of a parameter of the partial pressure specified for the first gas by the gas flow data set. The parameter may include a maximum value, a mean, a median, and/or other parameters. In some embodiments, operation 66 may be performed by a baseline flow rate module similar to or the same as baseline flow rate module 36 (shown in FIG. 1 and described above).

At an operation 68, a first flow rate for the first gas is determined. The first flow rate is determined based on the partial pressure specified for the first gas by the gas flow data set. The first flow rate is determined such that the first flow rate changes over time in accordance with the partial pressure specified for the first gas by the gas flow data set. In some embodiments, operation 68 is performed by a first flow rate module similar to or the same as first flow rate module 38 (shown in FIG. 1 and described above).

At an operation 70, the pressurized flow of gas specified by the gas flow data set is generated. This includes delivering the baseline gas at the baseline flow rate and delivering the first gas at the first flow rate to simulate the pressurized flow of gas specified by the gas flow data set. In some embodiments, operation 70 is performed by a control module similar to or the same as control module 42 (shown in FIG. 1 and described above) controlling a flow generator similar to or the same as flow generator 19 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to generate a simulated pressurized flow of gas including a first gas having a partial pressure that varies in a predetermined manner to simulate a respiratory as flow of a subject, the system comprising:

electronic storage which has stored therein a gas flow data set that comprises a recorded plot of a pressurized flow of gas as a function of time representative of a respiratory gas flow of a subject exhibiting a respiratory phenomenon, state, event, or other respiratory circumstance, the gas flow data set specifying partial pressure of a first gas in the recorded plot of the pressurized flow of gas as a function of time;

an outlet configured to emit a pressurized flow of gas;

a flow generator for generating the simulated pressurized flow of gas that simulates the respiratory gas flow of the subject, wherein the flow generator comprises:

a baseline valve assembly configured to control a flow rate of a baseline gas through the outlet; and a first valve assembly configured to control a flow rate of the first gas through the outlet; and one or more processors programmed to:

obtain a baseline flow rate for the baseline gas during generation of the simulated pressurized flow of gas, wherein the baseline flow rate is a function of a parameter of the partial pressure specified for the first gas from the gas flow data set;

determine a first flow rate for the first gas based on the partial pressure specified for the first gas from the gas flow data set such that the first flow rate changes over time in accordance with the partial pressure specified for the first gas from the gas flow data set; and control the flow generator to generate the simulated pressurized flow of gas that simulates the respiratory gas flow of the subject represented by the gas flow data set, including controlling the baseline valve assembly to deliver the baseline gas to the outlet at the baseline flow rate and controlling the first valve assembly to deliver the first gas to the outlet at the first flow rate.

2. The system of claim 1, wherein the one or more processors is programmed to obtain the baseline flow rate as a constant baseline flow rate during generation of the simulated pressurized flow of gas.

3. The system of claim 1, wherein the parameter of the partial pressure specified for the first gas from the gas flow data set used to determine the baseline flow rate comprises one or more of a maximum first partial pressure, a mean partial pressure, or a median partial pressure.

4. The system of claim 1, wherein the one or more processors is programmed to obtain the baseline flow rate for the baseline gas comprising a mixture of gases that does not include the first gas.

5. The system of claim 1, wherein the gas flow data set specifies the partial pressure of either carbon dioxide or oxygen in the recorded plot of the pressurized flow of gas as a function of time.

6. A system for generating a simulated pressurized flow of gas including a first gas having a partial pressure that varies in a predetermined manner to simulate a respiratory gas flow of a subject, the system comprising:

means which has stored therein a gas flow data set that comprises a recorded plot of a pressurized flow of gas as a function of time representative of a respiratory phenomenon, state, event or other respiratory circumstance, the gas flow data set specifying partial pressure of a first gas in the recorded plot of the pressurized flow of gas as a function of time; and means for generating the simulated pressurized flow of gas that simulates the respiratory gas flow of the subject in accordance with the gas flow data set such that the partial pressure of the first gas varies over time as specified in the gas flow data set, wherein the means for generating the pressurized flow of gas comprises:

means for obtaining a baseline flow rate for a baseline gas during generation of the simulated pressurized flow of gas, wherein the baseline flow rate is a function of a parameter of the partial pressure specified for the first gas from the gas flow data set;

means for determining a first flow rate for the first gas based on the partial pressure specified for the first gas from the gas flow data set such that the first flow rate changes over time in accordance with the partial pressure specified for the first gas from the gas flow data set; and means for delivering the baseline gas at the baseline flow rate and the first gas at the first flow rate to create the pressurized flow of gas specified by the gas flow data set.

7. The system of claim 6, wherein the baseline flow rate is constant during generation of the simulated pressurized flow of gas.

8. The system of claim 6, wherein the parameter of the partial pressure specified for the first gas from the gas flow data set used to determine the baseline flow rate comprises one or more of a maximum first partial pressure, a mean partial pressure, or a median partial pressure.

9. The system of claim 6, wherein the baseline flow rate module is configured to obtain a baseline flow rate for the baseline gas comprising a mixture of gases that does not include the first gas.

10. The system of claim 6, wherein the gas flow data set specifies the partial pressure of either carbon dioxide or oxygen in the recorded plot of the pressurized flow of gas as a function of time.

11. The system of claim 6, wherein the means for generating the pressurized flow of gas comprises:

means for controlling the means for generating the simulated pressurized flow of gas to generate the pressurized flow of gas that simulates the respiratory gas flow of the subject represented by the gas flow data set.

12. The system of claim 6, further including:

means for emitting a pressurized flow of gas to the means for generating the simulated pressurized flow of gas.

13. The system of claim 1, wherein the one or more processors is further programmed to:

determine a second flow rate for a first second gas based on a partial pressure specified for the second gas from the gas flow data set such that the second flow rate changes over time in accordance with the partial pressure specified for the second gas from the gas flow data set.

14. The system of claim 6, further including:

a means for determining a second flow rate for a first second gas based on a partial pressure specified for the second gas from the gas flow data set such that the second flow rate changes over time in accordance with the partial pressure specified for the second gas from the gas flow data set.

* * * * *